United States Patent [19]
Marin et al.

[11] Patent Number: 5,683,687
[45] Date of Patent: *Nov. 4, 1997

[54] INSECT ATTRACTANT COMPOSITIONS AND METHODS FOR USING SAME

[75] Inventors: Anna Belle Marin, Long Branch, N.J.; Jerry F. Butler, Gainesville, Fla.

[73] Assignees: International Flavors & Fragrances Inc., New York, N.Y.; The University of Florida, Gainesville, Fla.

[*] Notice: The portion of the term of this patent subsequent to Mar. 1, 2016, has been disclaimed.

[21] Appl. No.: 733,389

[22] Filed: Oct. 18, 1996

Related U.S. Application Data

[60] Continuation-in-part of Ser. No. 609,541, Mar. 1, 1996, Pat. No. 5,635,174, which is a division of Ser. No. 450,584, May 25, 1995, Pat. No. 5,635,173, which is a division of Ser. No. 241,555, May 12, 1994, which is a division of Ser. No. 130,256, Oct. 1, 1993, Pat. No. 5,401,500, which is a division of Ser. No. 948,142, Sep. 18, 1992, abandoned.

[51] Int. Cl.$^6$ .......................... A01N 65/00; A01N 25/00; A01N 25/08
[52] U.S. Cl. .......................... 424/84; 424/195.1; 424/405; 424/409; 424/486
[58] Field of Search .......................... 424/195.1, 84, 424/405, 409, 486

[56] References Cited

U.S. PATENT DOCUMENTS

| | | | |
|---|---|---|---|
| 4,970,068 | 11/1990 | Wilson et al. | 424/84 |
| 4,988,508 | 1/1991 | Wilson et al. | 424/84 |

FOREIGN PATENT DOCUMENTS

| | | |
|---|---|---|
| 1230826 | 12/1987 | Canada . |
| 8906904 | 8/1989 | WIPO . |

OTHER PUBLICATIONS

Atawia, et al, *Chemical Abstracts*, 1990, vol. 113:197620h, entitled "Effect of type of solvent on quantity and quality of jasmine concrete and absolute".

Thorsell, *Biological Abstracts*, vol. 88, No. 4, Aug. 15, 1989, abstract No. 36449, entitled "Introductory studies of plant extracts with mosquito repelling properties".

Beroza and Green, Materials Tested as Insect Attractants, Agriculture Handbook No. 239, Agricultural Research Service, U.S. Department of Agriculture, issued Jun. 1963, cover page and p. 112, Item Nos. 4612–4618: "lavandin oil" and lavender oil.

King, Chemicals Evaluated as Insecticides and Repellents at Orlando, Fla., published by Entomology Research Branch, U.S. Department of Agriculture, Agricultural Research Srvice, Agriculture Handbook No. 69, issed May 1954, two front cover pages and p. 188, Item No. 5712 (2-ethyl-1, 3-hexanediol).

Arctander, *Perfume and Flavor Materials of Natural Origin*, published by the author in 1960, front cover page and columns 309, 310, 311, 312, 339, 340, 341 and 342.

*Primary Examiner*—John Pak
*Attorney, Agent, or Firm*—Arthur L. Liberman

[57] ABSTRACT

Described are methods for attracting insects to a three-dimensional space inhabited by such insects comprising the step of exposing the three-dimensional space to an insect-attracting concentration and quantity of lavender absolute or jasmine absolute. More specifically, described is a method of attracting *Aedes aegypti* using lavender absolute; and a method of attracting *Musca domestica L.* (Diptera:Muscidae) using jasmine absolute. Also described are such methods of attracting insects to insect traps which contain the attractants jasmine absolute and/or lavender absolute as baits.

7 Claims, 10 Drawing Sheets

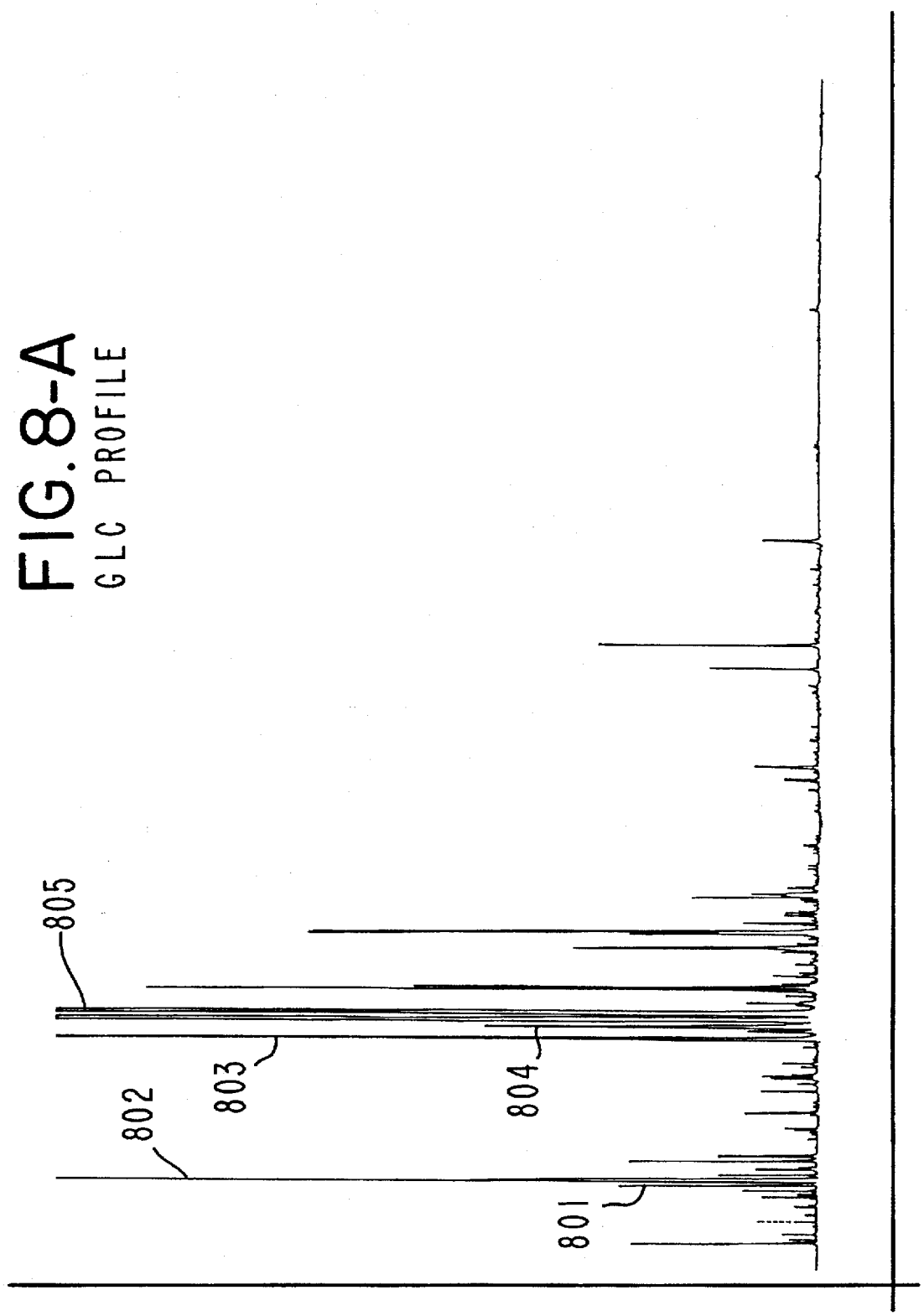

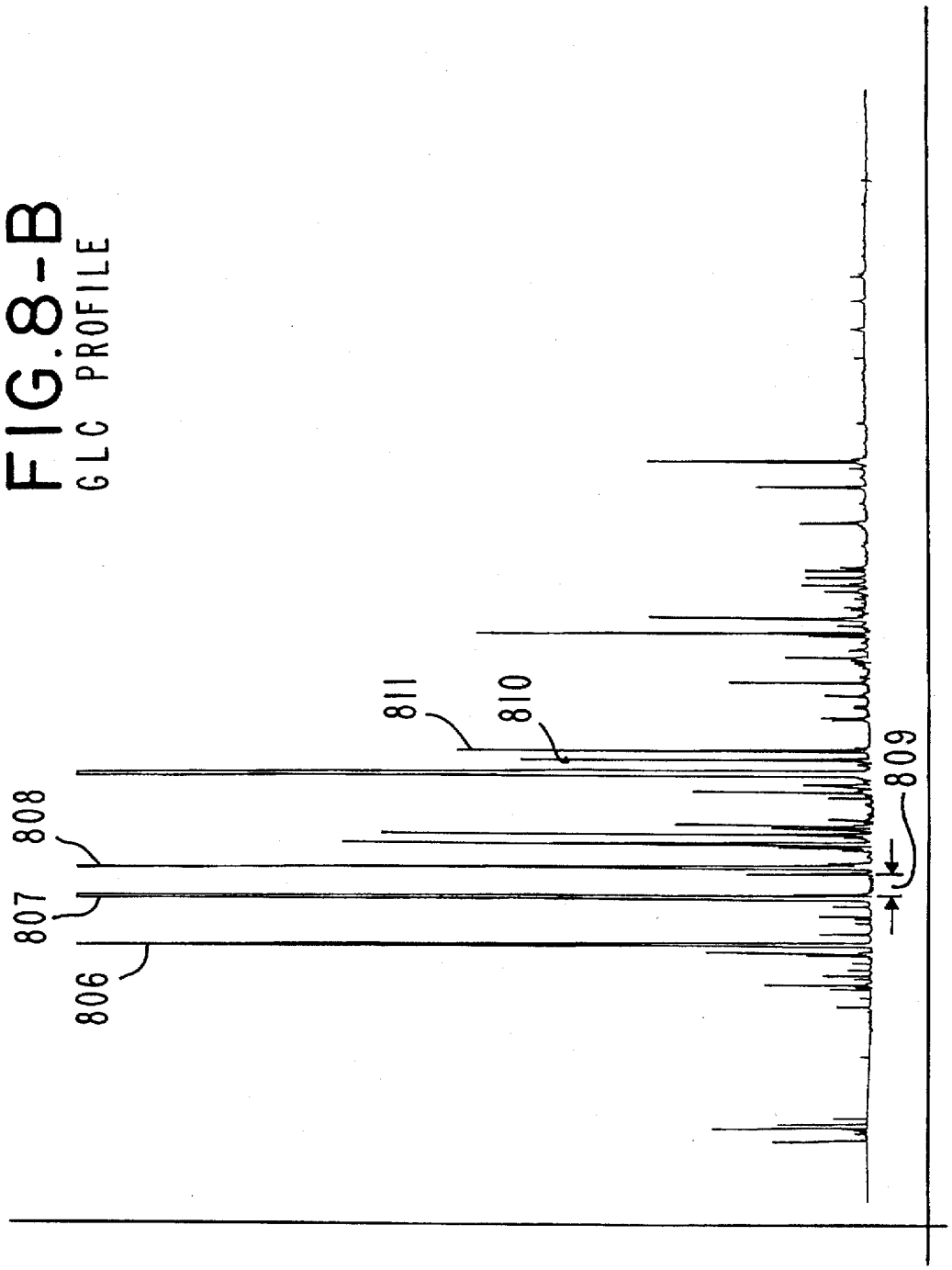
FIG. 8-B
GLC PROFILE

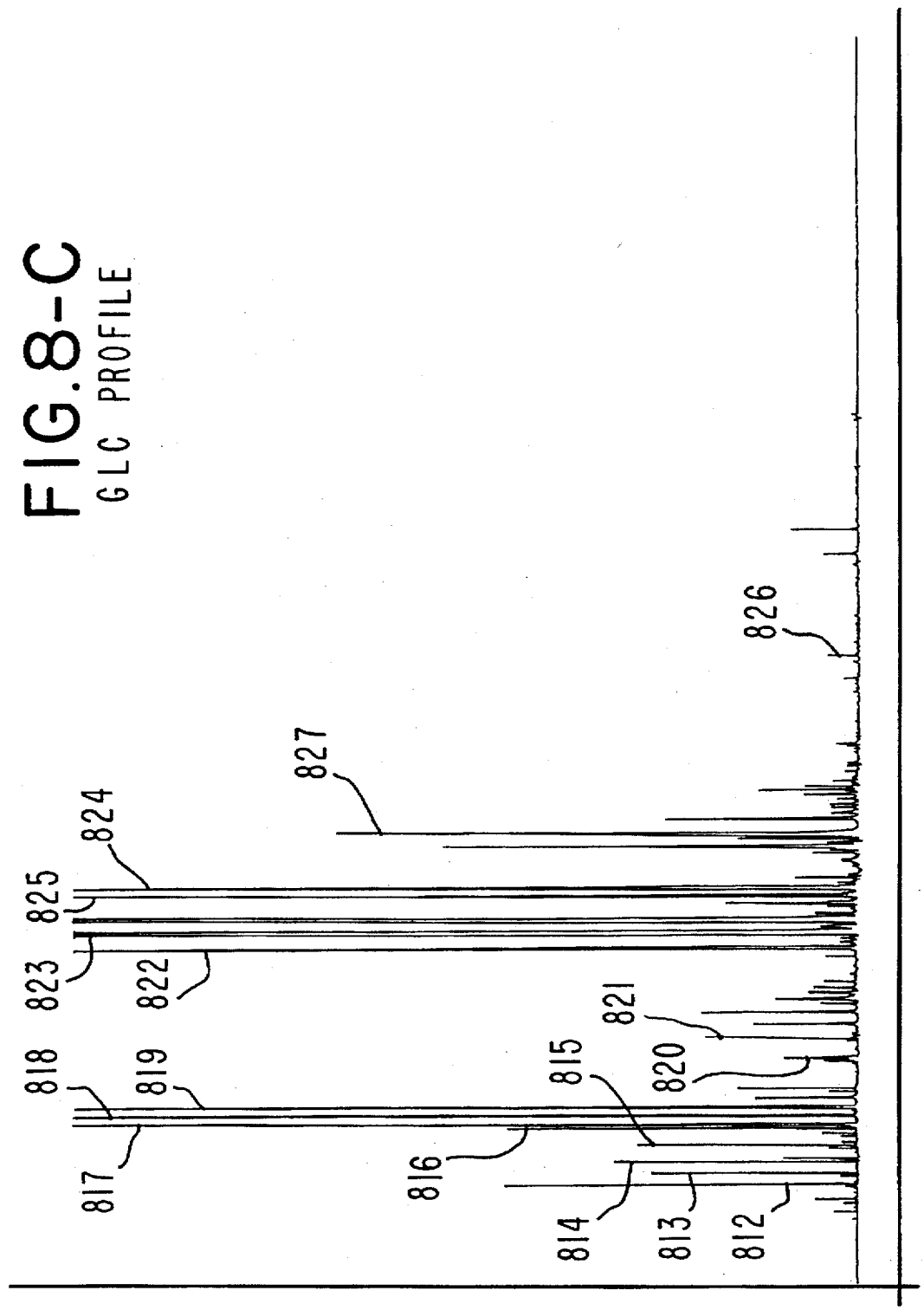

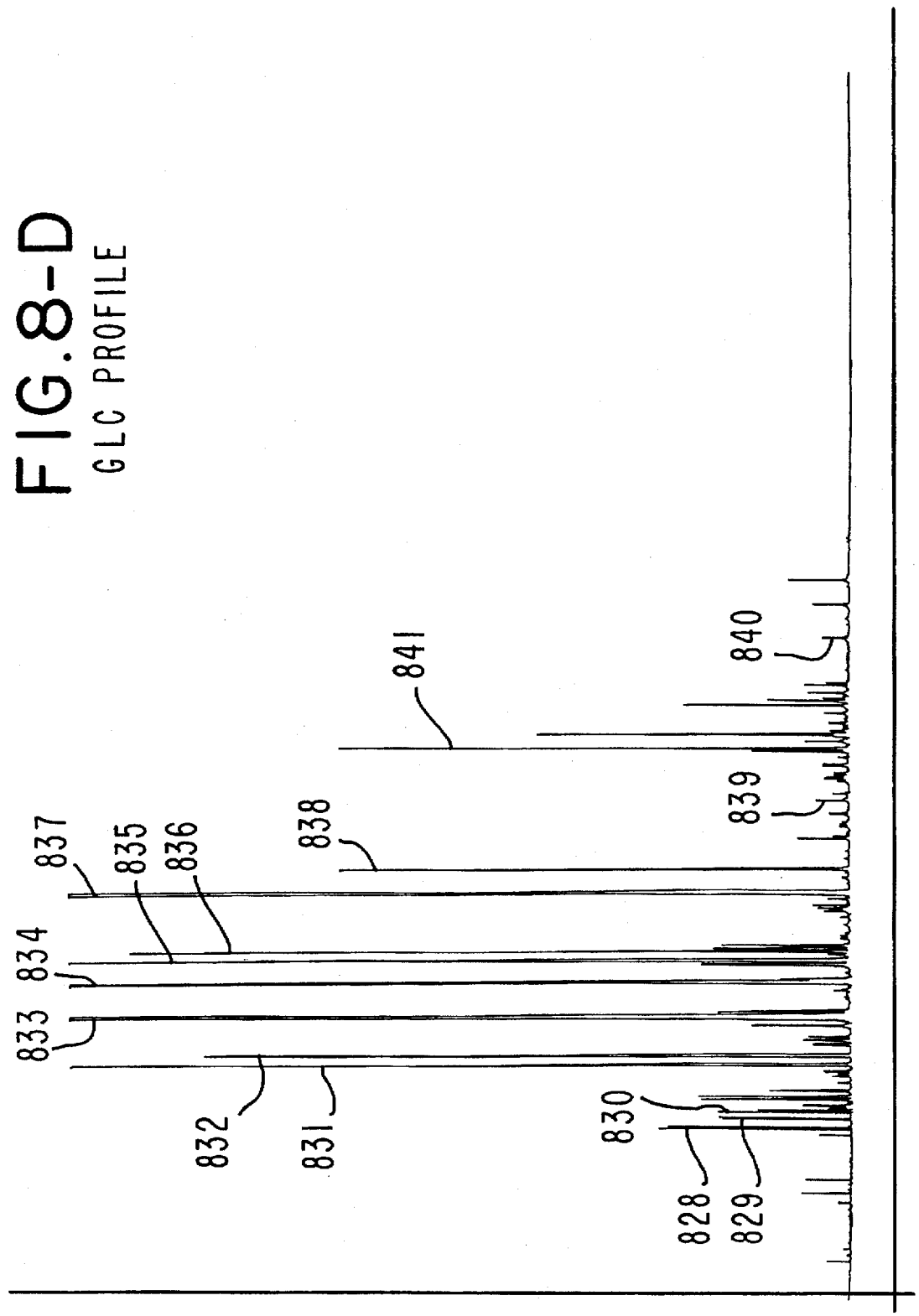

INSECT ATTRACTANT COMPOSITIONS AND METHODS FOR USING SAME

RELATED UNITED STATES PATENT APPLICATIONS

This Application is a Continuation-in-Part of U.S. patent application Ser. No. 08/609,541 filed on Mar. 1, 1996 now U.S. Pat. No. 5,635,174; which, in turn, is a Streamline Divisional of U.S. patent application Ser. No. 08/450,584 filed on May 25, 1995 now U.S. Pat. No. 5,635,173; which, in turn, is a Streamline Divisional of Application for U.S. patent Ser. No. 08/241,555 filed on May 12, 1994; which, in turn, is a Streamline Divisional of U.S. patent application Ser. No. 08/130,256 filed on Oct. 1, 1993, now U.S. Pat. No. 5,401,500 issued on Mar. 28, 1995; which, in turn, is a Streamline Divisional of U.S. patent application Ser. No. 07/948,142 filed on Sep. 18, 1992 (now abandoned).

BACKGROUND OF THE INVENTION

This invention relates to insect attractants for houseflies (*Musca domestica L.* (Diptera:Muscidae)) as well as mosquitoes (*Aedes aegypti*). More particularly, this invention relates to compositions of matter containing jasmine absolute or lavender absolute as attractants for *Musca domestica L.* (Diptera:Muscidae) and for *Aedes aegypti*. These attractants are useful as such or as contained in a polymer which can be a biodegradable polymer such as compositions containing major proportions of poly(epsilon caprolactone) homopolymers. The lavender absolute and jasmine absolute find utility primarily as bait enhancers for acute toxins and/or trapping devices.

Fast intercontinental travel and trade are stepping up changes of importing nonindigenous insect pests into the United States. Attractants, or lures, can be of considerable aid in facilitating the early detection of such insect pests, and they are of vital importance in measuring the progress of a program aimed at eradicating a species that has become established.

Beroza and Green, MATERIALS TESTED AS INSECT ATTRACTANTS, Agriculture Handbook No. 239, published by the United States Department of Agriculture, Agricultural Research Service (issued June 1963) discloses in Table 2 at Item Nos. 4612–4618, inclusive, the fact that lavandin oil as well as lavender oil attract the Oriental fruit fly, the melon fly, the Mediterranean fruit fly and the Mexican fruit fly at a level of "1" on a scale of "1–3". Nothing is indicated therein regarding the effectiveness as attractants of oil of lavandin or oil of lavender as housefly attractants. Nothing is set forth in Beroza and Green concerning the use of jasmine oil or jasmine absolute as housefly attractants.

Nothing in the prior art discloses the use of jasmine absolute or lavender absolute in attracting *Musca domestica L.* (Diptera:Muscidae) or in attracting *Aedes aegypti*.

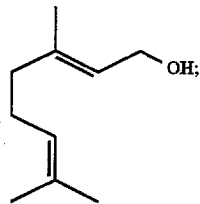

13.98 mole percent nerol having the structure:

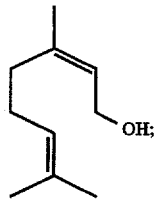

and 24.53 mole percent citronellol having the structure:

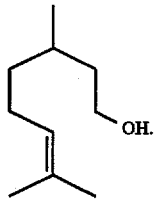

The graphs are based on experiments run for a period of 6 hours with six intervals of 1 hour each using as the insect to be tested the mosquito (*Aedes aegypti*). The results are tabulated in Table I, infra.

Figure 3:
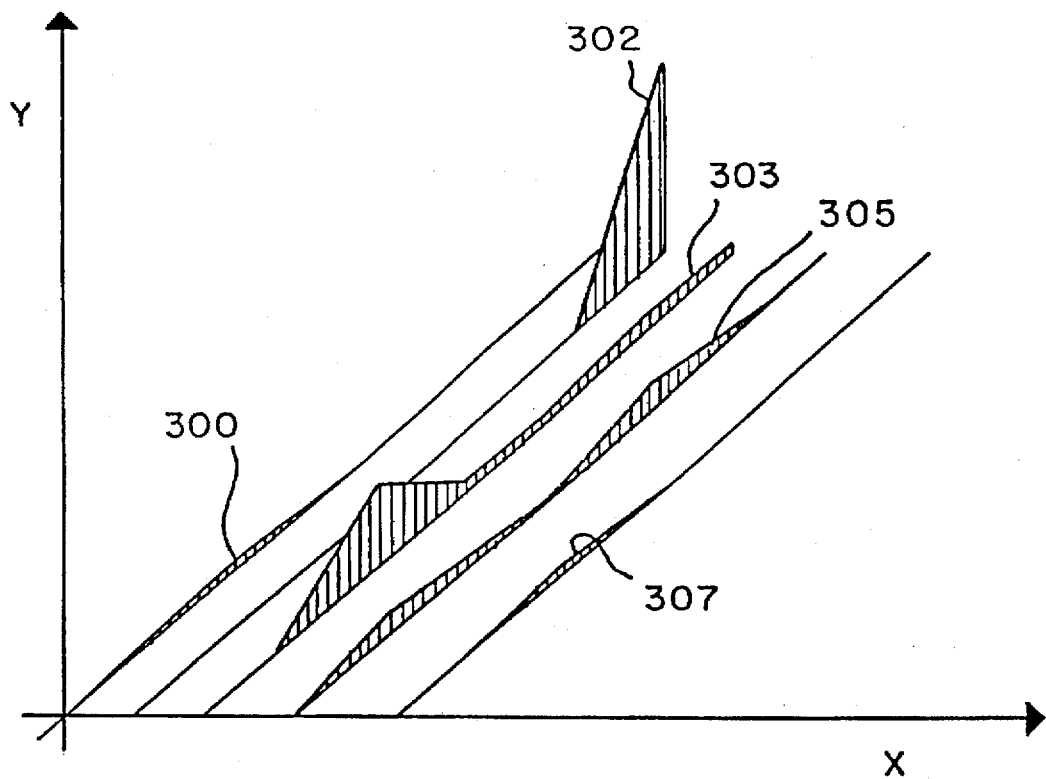

FIG. 3 is a series of graphs depicted in three dimensions (in a rectangular mode for the "X" and "Y" axes) showing the relative attractiveness or repellency of tridecene nitrile, air, jasmine absolute (having the GLC profile of FIG. 7, infra), dimethyl benzyl carbinyl acetate having the structure:

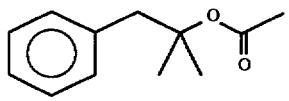

and a mixture containing 81.28 mole percent geraniol and 18.72 mole percent of a mixture of nerol and citronellol with the mole ratio of citronellol:nerol being 1.78. The graphs are based on experiments run for a period of 6 hours with six intervals of 1 hour each using as the insect to be tested the housefly, *Musca domestica L.* (Diptera:Muscidae). The results are tabulated in Table II, infra.

Figure 4:
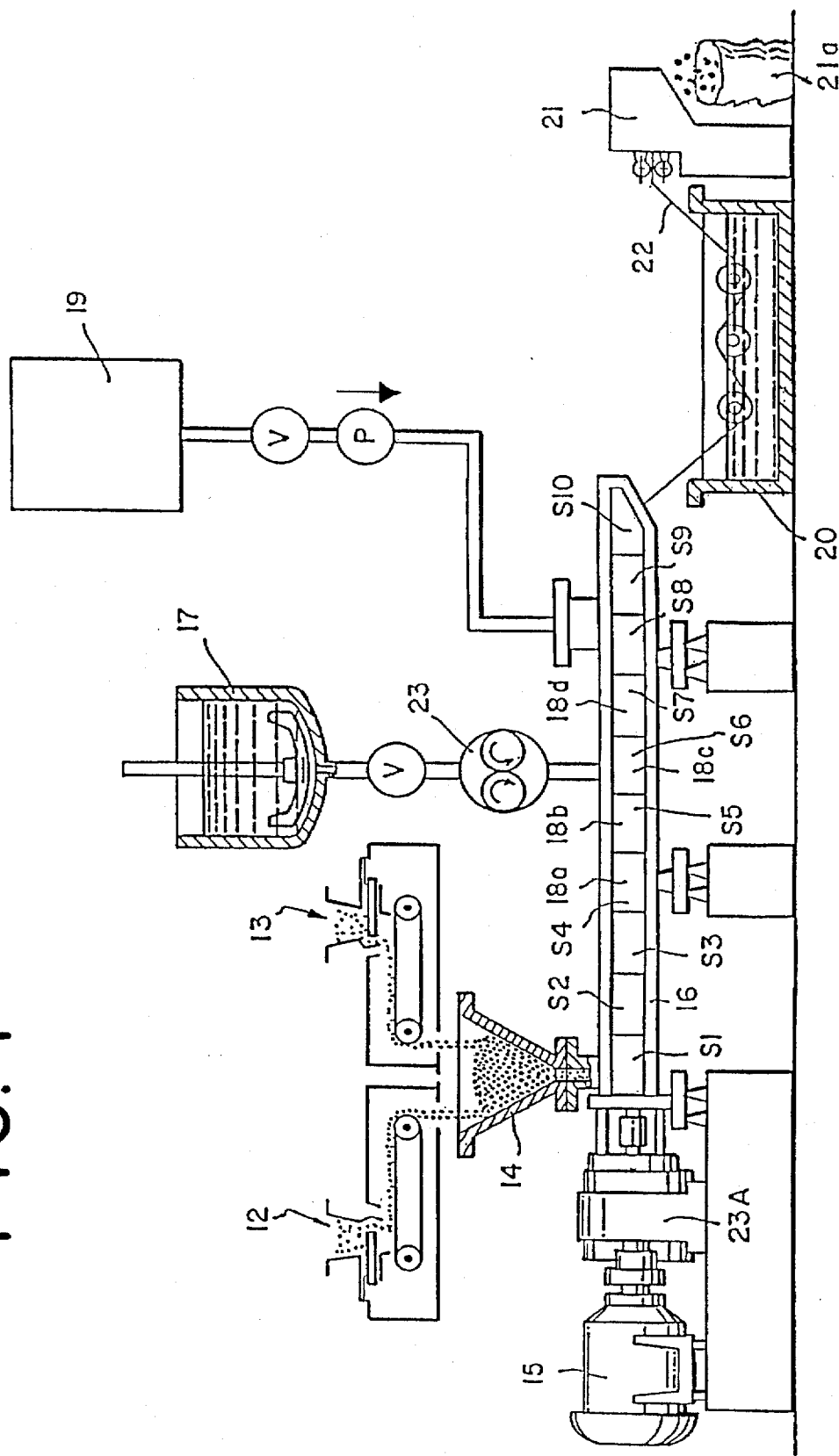

FIG. 4 is a cutaway side elevation schematic diagram of a screw extruder during the compounding of a resin with insect attractants including the materials:

lavender absolute and/or jasmine absolute while simultaneously adding a foaming agent into the hollow portion of the barrel of the extruder and incorporates the pelletizing apparatus used in the pelletizing of the extruded foamed tow produced as a result of the extrusion operation.

Figure 5:
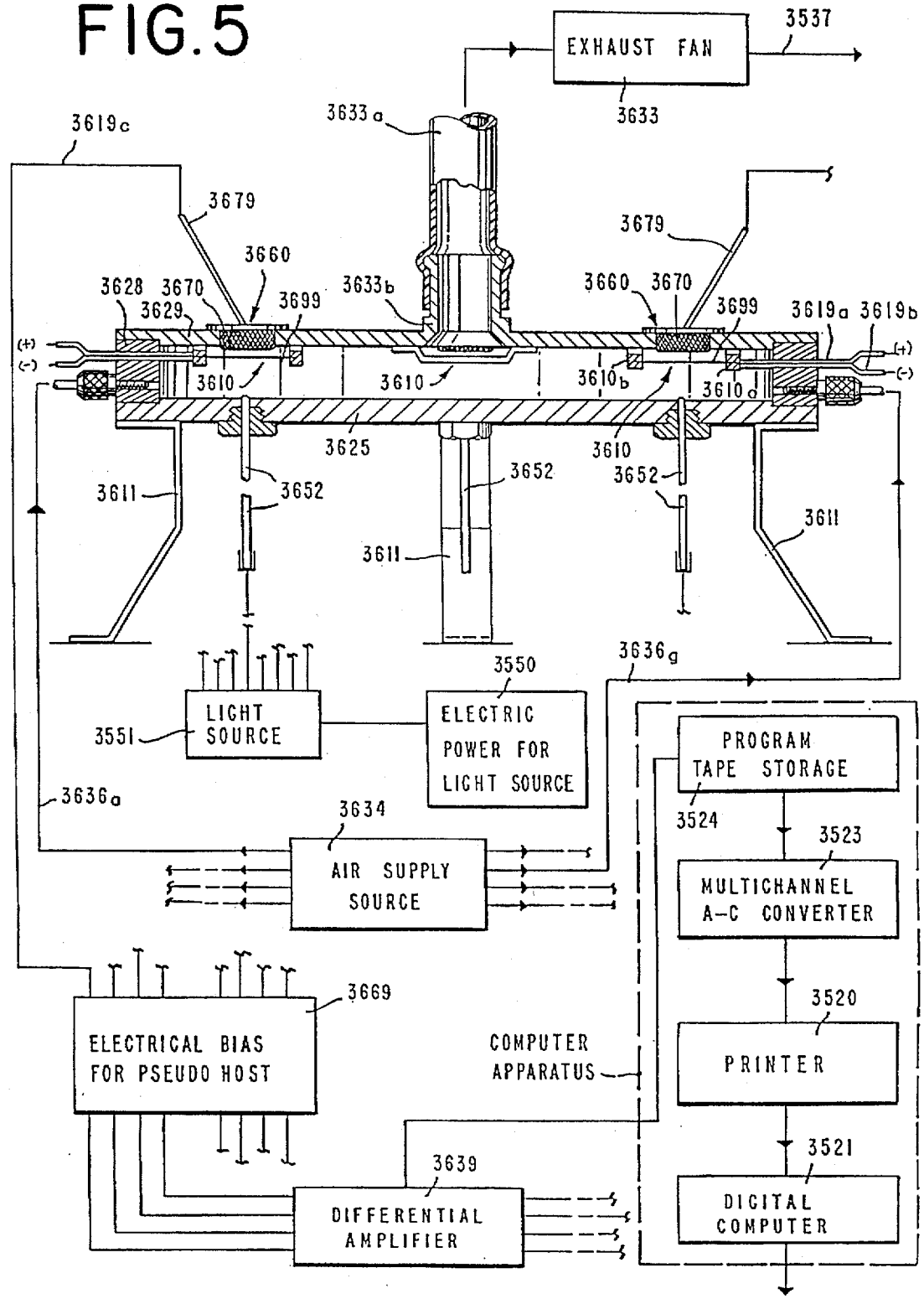

FIG. 5 is a cutaway side elevation view of the base section of the olfactometer apparatus used in carrying out the testing of the attractants of our invention indicating in the schematic block flow diagram form the utilization of computer-assisted efficacy measuring apparatus; but showing only an air supply entry into the side prots of the olfactometer apparatus with the treatment agent being contained in a control release matrix upstream from the air supply source.

Figure 6:
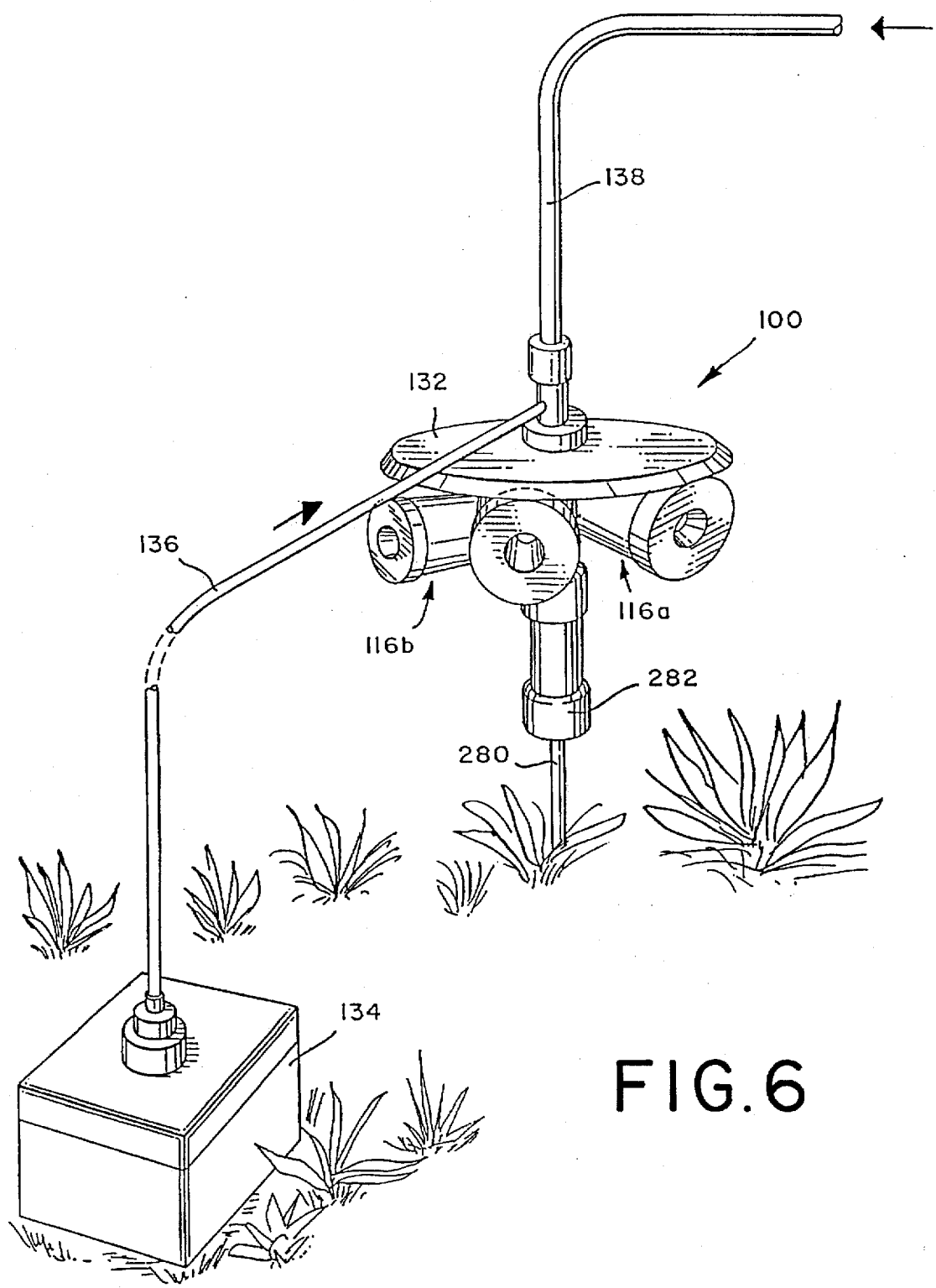

FIG. 6 is a perspective view of the semiochemical field trap for testing the attractiveness or repellency for blood feeding arthropods using the attractants of our invention which may be either lavender absolute or jasmine absolute. The semiochemical field trap is described in detail in U.S. Pat. No. 5,409,958 issued on Apr. 25, 1995, the specification for which is incorporated herein by reference.

Figure 7:
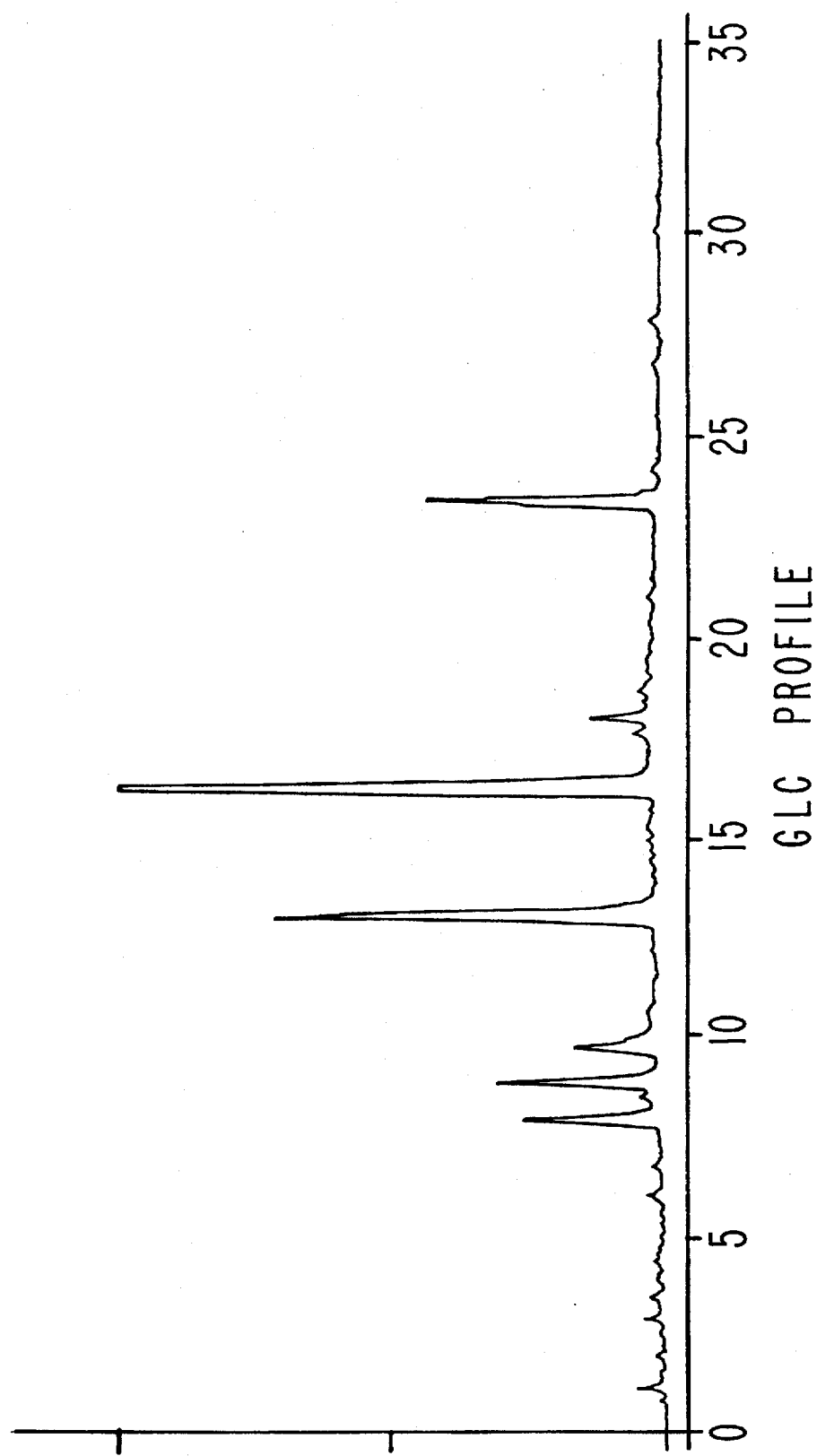

FIG. 7 is the GLC profile for the jasmine absolute prepared according to the process of Example I, infra.

FIG. 8A is the GLC profile for the lavender absolute prepared according to Example II (conditions: 60 meter dual-fused silica column coated with Carbowax 20M programmed from 70°–220° C. at 4° C. per minute).

FIG. 8B is the GLC profile for the lavender absolute prepared according to Example II (conditions: 50 meter dual-fused silica system/OV-1 column programmed from 70°–220° C. at 4° C. per minute).

FIG. 8C is the GLC profile for the lavender absolute prepared according to Example III (conditions: 50 meter dual-fused silica column coated with Carbowax 20M programmed from 70°–220° C. at 4° C. per minute).

FIG. 8D is the GLC profile for the lavender absolute prepared according to Example III (conditions: 50 meter dual-fused silica system/OV-1 column programmed from 70°–220° C. at 4° C. per minute).

SUMMARY OF THE INVENTION

This invention relates to the use of lavender absolute and jasmine absolute as attractants for houseflies (*Musca domestica L.* (Diptera:Muscidae)) and mosquitoes (*Aedes aegypti*).

Specifically, the lavender absolute has been found by us to be an attractant for mosquitoes (*Aedes aegypti*). The lavender absolute has been found to be an attractant for *Musca domestica L.* (Diptera:Muscidae). Mixtures of from 25% up to 75% by weight of lavender absolute and from 75% down to 25% by weight of jasmine absolute have been found to be attractants for both *Musca domestica L.* (Diptera:Muscidae) and mosquitoes (*Aedes aegypti*).

All forms of jasmine absolute as commercially available are useful as attractants as set forth, supra, for example:

(i) jasmine absolute Italian;

(ii) jasmine absolute Moroccan;

(iii) jasmine absolute pure;

(iv) JASMIN ABSOLUTE OLIFFAC® (as manufactured by International Flavors & Fragrances Inc.); and (v) JASMIN ABSOLUTE SPECIAL OLIFFAC® as manufactured by International Flavors & Fragrances Inc.).

A process for preparing jasmine absolute is set forth in Example I, infra, giving rise to the GLC spectrum described, supra. The jasmine absolute has the following specifications:

refractive index at 20° C. range: 1.508–1.524; and specific gravity at 25° C. range: 0.984–1.020.

All forms of commercially available lavender absolute are useful in the practice of our invention for attracting mosquitoes (*Aedes aegypti*), to wit:

lavender abrialis absolute;

lavender absolute colorless;

lavender absolute benzol poir;

lavender abrialis oil reconstituted (as manufactured by International Flavors & Fragrances Inc.); and LAVENDER OLIFFAC® (as manufactured by International Flavors & Fragrances Inc.).

The specifications for lavender absolute are as follows:

refractive index at 20° C. range: 1.453–1.464; and specific gravity at 25° C. range: 0.886–0.911.

Processes for producing lavender absolute are set forth in Examples II and III, infra. The GLC spectra for the lavender absolute of Examples II and III are set forth in FIGS. 8A and 8B (Example II) and FIGS. 8C and 8D (Example III).

Our invention also relates to the use of lavender absolute or jasmine absolute in specific trapping systems. A trapping system which is the basis of a testing technique used in testing the efficacy of jasmine absolute and lavender absolute and combinations thereof is a standard ZOECON® sticky trap consisting of a ZOECON PHEROCON® 1C trap with a 2 cm×2 cm strip of formulated, slow release attractant suspended on a paper clip inside the trap. The traps were placed in a goat barn and were suspended from the rafters. Trap placement was replicated in the four quadrants of the barn. Traps were placed in the barn for seven days and the insects collected were identified and counted. Evidence of insects visiting the traps were also counted as insect specks inside or outside the traps. All test materials were compared with a standardized check treatment consisting of 0.5 grams of GOLDEN MALRIN® fly bait inside the slow release packet hung like other compounds.

Our invention also relates to the formation of insect attractant-containing polymeric pellets by means of introduction into a single screw or twin screw extruder of, in series, thermoplastic polymer followed by insect attractant (that is, lavender absolute or jasmine absolute) which is compatible with the thermoplastic polymer, in turn, followed by introduction of a gaseous blowing agent or blowing agent which will produce a gas which is inert to the polymer and to the insect attractant, e.g., jasmine absolute, lavender absolute or combinations thereof.

In the alternative, the use of a foaming agent can be omitted.

The nature of the extruder utilized in this aspect of our invention to form the polymeric insect attractant particles of our invention may be either single screw or double screw. Thus, the types of extruder that can be used are disclosed at pages 246–267 and 332–349 of the *Modern Plastics Encyclopedia*, 1982–1983, published by the McGraw-Hill Publishing Company, the disclosure of which is incorporated by reference herein. More specifically, examples of extruders which are usable in carrying out this aspect of our invention (with modification for introduction of the polymer and, optionally, with a further modification that the gaseous blowing agent is introduced still further downstream from the point of introduction of insect attractant) are as follows:

1. The Welex "Super Twinch" 3.5 inch extruder, manufactured by Welex Incorporated, 850 Jolly Road, Blue Bell, Pa. 19422;

2. Krauss-Maffei twin screw extruder, manufactured by the Krauss-Maffei Corporation/Extruder Division, 3629 West 30th Street South, Wichita, Kans. 67277;

3. Modified Sterling Model 4000 and 5000 series extruder, manufactured by the Sterling Extruder Corporation of 901 Durham Avenue, South Plainfield, N.J.;

4. CRT ("Counter-Rotating Tangential") Twin Screw Extruder, manufactured by Welding Engineers, Inc. of King of Prussia, Pa. 19406;

5. The Leistritz Twin Screw Dispersion Compounder, manufactured by the American Leistritz Extruder Corporation of 198 U.S. Route 206 South, Somerville, N.J. 08876;

6. The ZSK Twin Screw Co-Rotating Extruder, manufactured by the Werner & Pfleiderer Corporation of 663 East Crescent Avenue, Ramsey, N.J. 07446;
7. The Farrel Extruder, manufactured by the Farrel Connecticut Division, Emhart Machinery Group, Ansonia, Conn. 06401;
8. The MPC/V Baker Perkins Twin Screw Extruder, manufactured by the Baker Perkins Inc. Chemical Machinery Division of Saginaw, Mich. 48601; and
9. The Berstorff Single Screw, Twin Screw, or Foam Extrusion Equipment, manufactured by the Berstorff Corporation, P.O. Box 240357, 8200-A Arrowridge Boulevard, Charlotte, N.C. 28224.

In producing the insect attractant-containing polymer particles of our invention, various polymers may be utilized, for example, low density polyethylene, high density polyethylene, polypropylene, the copolymer of ethylene and acetate, and polyvinyl chloride. More specifically, the polymers used in the practice of our invention may be copolymers of ethylene and a polar vinyl monomer selected from (a) vinyl acetate; (b) ethyl acrylate; (c) methyl acrylate; (d) butyl acrylate; and (e) acrylic acid including the hydrolyzed copolymer of ethylene and vinyl acetate. Preferred copolymers are ethylene vinyl acetate with about 9 to 60% vinyl acetate and ethylene/ethyl acrylate with about 6 to 18% ethyl acrylate.

Resins of the type disclosed for use as copolymers are commercially available in the molding powder form. For example, ethylene vinyl acetate copolymers are marketed by the O.D.E.I. duPont de Nemours Company under the tradename "ELVAX®" and by the Arco Polymer Division under the trademark "DYLAND®" and by the Exxon Corporation of Linden, N.J. under the trademark "DEXXON®". Ethylene/ethyl acrylate copolymers are marketed by the Union Carbide Corporation under the tradename "EEA RESINS®".

The polymer is added to the single screw or twin screw extruder at a feed rate in the range of from about 80 up to about 300 pounds per hour while maintaining the temperature in the screw extruder between about 160° C. and 240° C. If the polymer or copolymer powder is added to the extruder at a reference "barrel segment", then the insect attractant is added to the extruder under pressure downstream from the addition point of the polymer at 1 or more "barrel segments" S-2, S-3, S-4, S-5, S-6, S-7, S-8 or S-9.

Thus, the invention provides a process for forming insect attractant-containing polymeric particles such as polymeric pellets which include a relatively high concentration of insect attractants. The insect attractant added at "barrel segments" S-2, S-3, S-4, S-5, S-6, S-7, S-8 or S-9 of the single screw or twin screw extruder is to be compatible with the polymer added at "barrel segment" S-1 of the single screw or twin screw extruder.

The proportion of insect attractant is limited only by either (a) its solubility in the resin or mixture of resins used and/or (b) the volume ratio of microvoids in the polymer to said polymer and/or (c) the solubility of the insect attractant in the polymer on solidification. The proportion of insect attractant can, in many instances, go up to 45% by weight or even higher.

Thus, the proportion of insect attractant to resin can vary from small but effective amounts on the order of about 1% of the weight of the resin body up to about 45% by weight of the resin body. In general, it is preferred to use between about 5% up to about 30% based on the weight of the resin body of the insect attractant. This is an optimum amount balancing the proportion of insect attractant against the time period over which the article emits the insect attractant and against the tendency of the insect attractant to "oil out". This "oiling out" is specifically avoided as a result of the use of foaming agent.

As stated, supra, various polymers are useful in the practice of our invention. Specific examples of polymers useful in the practice of our invention are as follows:

(a) DYLAN® brand of low density polyethylene. DYLAN® is a trademark owned by the Atlantic Richfield Company of Los Angeles, Calif.;

(b) DYLITE® of expandable polystyrene compositions. DYLITE® is a trademark of the Atlantic Richfield Company of Los Angeles, Calif.;

(c) SUPER DYLAN®, a high density polyethylene. SUPER DYLAN® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/α-olefin as exemplified and disclosed in U.S. Pat. No. 4,369,291, the specification for which is incorporated by reference herein;

(g) Poly-α-olefins as exemplified in Canadian Letters Patent No. 1,137,069 issued on Dec. 7, 1982, the specification for which is incorporated by reference herein;

(h) Polymeric compositions as disclosed in Canadian Letters Patent No. 1,137,068 issued on Dec. 7, 1982, the specification for which is incorporated by reference herein;

(i) Poly-α-olefins disclosed in Canadian Letters Patent No. 1,137,067, the specification for which is incorporated by reference herein;

(j) Polyolefins described in Canadian Letters Patent No. 1,137,066, the specification for which is incorporated by reference herein;

(k) Polyethylene oxides as disclosed in Canadian Letters Patent No. 1,137,065 issued on Dec. 7, 1982, the specification for which is incorporated by reference herein;

(l) Olefin polymers and copolymers as disclosed in Canadian Letters Patent No. 1,139,737 issued on Jan. 18, 1983, the disclosure of which is incorporated by reference herein;

(m) Polyolefins disclosed in Canadian Letters Patent No. 1,139,738 issued on Jan. 18, 1983, the disclosure of which is incorporated by reference herein;

(n) Chlorinated PVC as disclosed in *Polymer* 1982, 23 (7, suppl.), pages 1051–1056, abstracted in *Chemical Abstracts*, Volume 97:145570y, 1982;

(o) Polyepsilon caprolactone copolymers made by means of alcohol initiated polymerization as disclosed in *J. Polym. Sci., Polym. Chem. Ed.* 1982, 20(2), pages 319–326, abstracted at *Chemical Abstracts*, Volume 96:123625x, 1982;

(p) Styrene acrylonitrile copolymers as disclosed in *Diss. Abstracts, Int. B*, 1982, 42(8), 3346 and abstracted at *Chemical Abstracts*, Volume 96:143750n (1982);

(q) Copolymers of epsilon caprolactone with 1,4-butane diol as disclosed at *Kauch. Rezine*, 1982 (2), pages 8–9, abstracted at *Chemical Abstracts*, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, *J. Polym. Sci., Polym. Phys. Ed.* 1982, 20(2), pages 191–203;

(t) Plasticized polyepsilon caprolactone copolymers containing dimethyl phthalate plasticizers as set forth in Japanese Patent No. J81/147844, abstracted at *Chemical Abstracts*, Volume 96:69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long-chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Optionally, downstream from the addition point of the insect attractant, a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed insect attractant-containing polymer particle.

The feed rate of insect attractant may be between about 0.5% up to about 45% by weight of the polymer.

The die of the extruder may create rod, sheet, film or ribbon. The resulting product may then, if desired, be pelletized to form foamed insect attractant-containing polymer particles or the ribbon may be used "as is" as an insect attractant-containing polymeric article of manufacture itself.

In addition to the optional gaseous blowing agents (which are necessarily "inert" gases), blowing agents may be added at some point on the extruder which will create gaseous voids in the insect attractant-containing polymeric articles of our invention, and these "blowing agents" are well known to one having ordinary skill in the art. Examples of such non-gaseous containing materials which yield gases on admixture with the polymer in the extruder but which are still inert to the insect attractant are as follows:

(i) under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$, separately or in admixture with one another as set forth in U.S. Pat. No. 3,758,425, column 4, lines 1–5, the specification for which is incorporated by reference herein;

(iii) dichlorotetrafluoroethane, tetramethylmethane, monochlorodifluoromethane, dichlorodifluoromethane and dichlorotetrafluoroethane as specifically described in U.S. Pat. Nos. 2,948,664 and 2,948,665 issued on Aug. 9, 1960, the specification for which is incorporated by reference herein; and (iv) Axo bis(formamide); diazoaminobenzene; N,N'-dinitrosopentamethylene tetramine; N,N'-dimethyl-N, N'-dinitrosoterephthalamide; p,p'-oxy-bis(benzene sulfonyl semi-carbazide); azo bis(isobutyronitrile); p,p'-oxy-bis(benzene sulfonyl hydrazide); p,p'-diphenyl-bis (sulfonyl hydrazide); benzenesulfonyl hydrazide; m-benzene-bis(sulfonyl hydrazide), as more specifically described in U.S. Pat. No. 3,298,975 issued on Jan. 17, 1967, the specification for which is incorporated by reference herein.

The resulting extruded (and, if desired, pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

Figure 1:
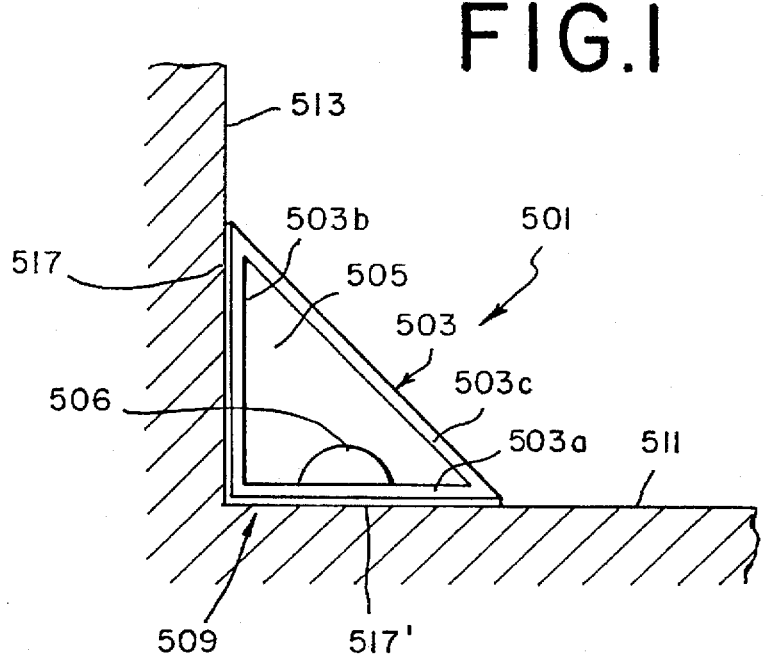
FIG. 1 is a cutaway side elevation view of a poisonous bait container for crawling insects useful in carrying out the process of our invention and useful for containing a poisonous bait which contains jasmine absolute or lavender absolute for attracting *Aedes aegypti* or *Musca domestica L.* (Diptera:Muscidae) into the trap.

Referring to FIG. 1, FIG. 1 sets forth a poisonous bait container for insects such as *Musca domestica L.* (Diptera:Muscidae) as well as *Aedes aegypti* or volumes infested with both *Aedes aegypti* and *Musca domestica L.* (Diptera:Muscidae). FIG. 1 sets forth the container disclosed and claimed in U.S. Pat. No. 5,531,043 issued on Jul. 2, 1996, the specification for which is incorporated by reference herein. FIG. 1 shows a poisonous bait container 501 for crawling insects consisting of a body 517/517' consisting of first, second and third walls 503a, 503b and 503c, respectively; having a triangular cross-sectional shape, the first and second walls being in substantially perpendicular relation to one another (that is, wall 503b being perpendicular to wall 503a) and each having a width not greater than 2 cm resting on surface 511 and buttressed against wall 513 having an inner void 505 and having on its surface 503a a poisonous bait 506 containing either or both of the jasmine absolute and/or the lavender absolute. The ledge 511 on which the container is resting is the surface of a solid foundation 509. Adhesive means on ledge 511 at 517' and at wall 513 at location 517 hold the container in place. Adhesive means could also hold the poisonous bait-holding polymer (insect control means) 506 in place.

Figure 2:
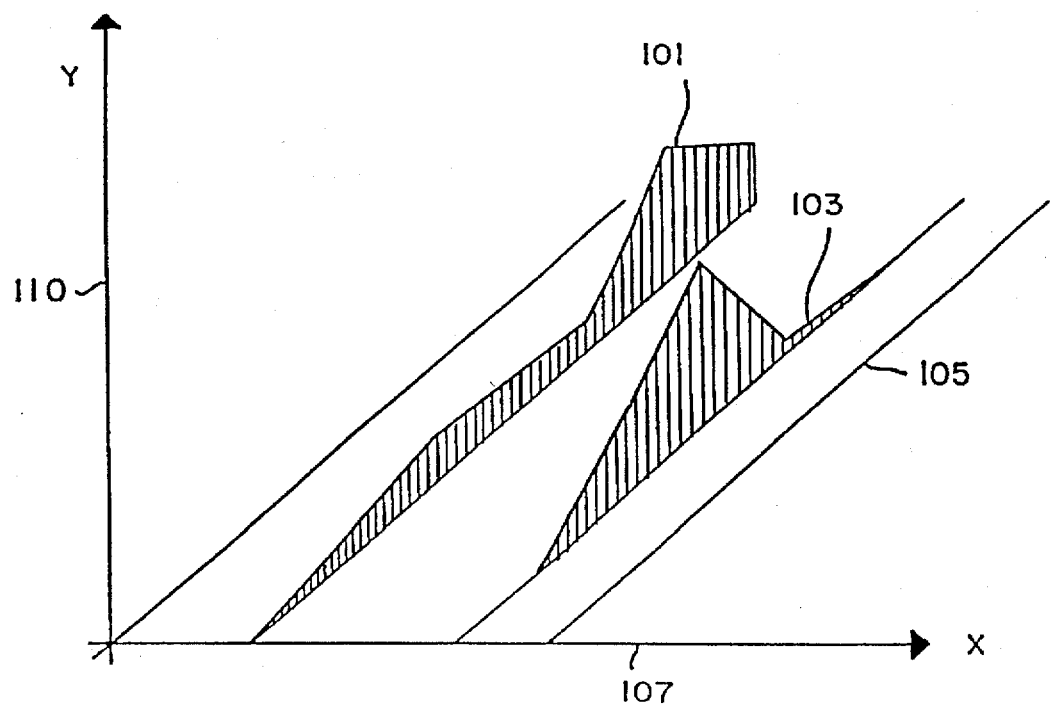
FIG. 2 is a series of graphs depicted in three dimensions (in a rectangular mode for the "X" and "Y" axes) showing the relative attractiveness or repellency of air, lavender absolute (having the GLC profile of FIG. 8C) and a mixture of geraniol, citronellol and nerol containing 61.49 mole percent geraniol having the structure.

The data set forth in FIGS. 2 and 3 were determined using the olfactometer of FIG. 5 and the insect trap of FIG. 6. Referring to the olfactometer of FIG. 5, said olfactometer is described in detail in U.S. Pat. No. 5,118,711 issued on Jun. 2, 1992, the specification for which is incorporated by reference herein.

Referring to FIG. 5, air supply source 3634 provides air to a mixing station 3636 wherein the air is mixed with treatment agent from treatment agent source 3635 (source of, for example, the repellent a 50–100% geraniol-containing composition or the attractant, lavender absolute). The resulting mixture passes through tube 3636g and enters the apparatus through the side portals. The entry is through a spacer plate and above base plate 3625. The entry of the air-treatment agent is in a direction parallel to the surface of base plate 3625. Thus, the base plate 3625 is separated from spacer plate 3629 for the air-treatment agent (e.g., the lavender absolute-containing composition of our invention).

Air exits through line 3633a using exhaust fan 3633. The air exit is indicated by reference numeral 3537.

Simultaneously, with the supplying of air and treatment agent from mixing station 3636, light is supplied from beneath the enclosed insect feeding and/or stimulating means through light guides 3652, from light source 3551 which is powered by Division of Tandy Corporation of Forth Worth, Texas 76102 under electric power supply 3550 marketed by RADIO SHACK®, the trademark ARCHER®, Catalog No. 276-228 ("1.0 mm optical plastic fiber length 5 meter"). An example of light source 3551 is KRATOS Monochromatic Illuminator GM 100 Miniature VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source from location 3634 and treatment agent from location 3635 is mixed at mixing station 3636 whereupon treatment agent and air in admixture is passed through lines 3636a and 3636g through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628. It should be noted that the spacer plate 3629, spacer ring 3628 and base plate 3625 enclose the entire "enclosed insect feeding and/or stimulating means" which have controlled limited access to the external environment surrounding the apparatus and in which the insects to be tested, e.g., mosquitoes or houseflies are placed.

The insect attractant quantitative detecting means made up of wires 3699 (the entire grid being denoted using reference numeral 3610) is located immediately beneath the porous membrane 3670, the outer surface of which contains a feeding stimulant composition or stimulant composition for insects (for example, agar). Immersed in the feeding stimulant composition or stimulant composition for insects (e.g., agar) is electrode 3679 connected to wire 3619 which connects with either wire 3619a or 3619b which is connected to the grid wires 3699 (which make up the insect attractant quantitative detecting means located immediately below lamina 3670).

As state, supra, the sensor causes an electrical impulse caused by the pressure of the insects landing to proceed through wires 3619a and 3619b to an electrically biased differential amplifier 3639 (using electrical power supply 3539) also connected to wire 3619c which is connected to the electrode 3679 which is immersed in the feeding stimulant composition or stimulant for the insect and then to a multichannel A-C converter 3523. Converter 3523 is associated with program tape storage 3524, printer 3520 and data link to digital computer 3521. Differential amplifier 3639 is connected in series to electrical bias for pseudo host 3669 which in turn is connected to wire 3619 which in turn is connected to the electrode 3679 immersed in the insect stimulant composition located on the surface of porous lamina 3670.

Referring to the testing apparatus, the semiochemical field trap 100 for blood feeding arthropods, field trap 100 is located in a three space with axes perpendicular to one another. The semiochemical field trap 100 is shown in a perspective view in FIG. 6 comprising:

(1) an upright, vertically disposed housing;
(2) extending outwardly from the housing, a plurality of horizontally disposed hollow housings 116a and 116b which have contained therein insect sticky traps;
(3) air 138 and/or carbon dioxide supply means 134 and 136 for supplying air and/or carbon dioxide into the vertical hollow housing and then through the plurality of horizontally disposed hollow housings 116a and 116b; and
(4) at least one power supply means for energizing radiation means located on the vertical hollow housing whereby, on engagement of the power supply means with the radiation means and operation of the air 138 and/or carbon dioxide supply means 134 and 136, arthropods in the vicinity of the trap are attracted by the activated radiation means and the gas emanating from the horizontally disposed hollow housing 116a to a location so close to the trap 100 that, in the event that an attracting semiochemical located in the housings 116a and 116b is detected by at least one of the arthropods, at least one of the arthropods will enter the inner void of the horizontally disposed hollow housings 116a and 116b counter current, the gas stream emanating therefrom and remain permanently entrapped therein.

The semiochemical field trap 100 of FIG. 6 is disclosed in detail in U.S. Pat. No. 5,409,958 issued on Apr. 25, 1995, the specification for which is incorporated by reference herein.

FIG. 2 is a series of graphs depicted in three dimensions (in a rectangular mode for the "X" and "Y" axes) showing the relative attractiveness or repellency of air, lavender absolute (having the GLC profiles of FIGS. 8C and 8D prepared according to Example III, infra) and a mixture containing 61.49 mole percent geraniol, 13.98 mole percent nerol and 24.53 mole percent citronellol with respect to attractiveness or repellency of *Aedes aegypti*. The graph indicated by reference numeral 101 is for air. The graph indicated by reference numeral 103 is for lavender absolute. The graph indicated by reference numeral 105 is for the mixture containing 61.49 mole percent geraniol, 13.98 mole percent nerol and 24.53 mole percent citronellol. The "X" axis along which the particular materials are measured insofar as their attractiveness or repellency is concerned is indicated by reference numeral 107. The number of insects collected per interval is indicated on the "Y" axis and the "Y" axis is indicated by reference numeral 110. The results are tabulated in Table I as follows:

TABLE I

| Composition Tested | Graph No. | Insects Collected Per Interval | | | | | | |
|---|---|---|---|---|---|---|---|---|
| Geraniol/Nerol/Citronellol Mixture | 105 | 0 | 3 | 1 | 0 | 0 | 0 | 0 |
| Air | 101 | 0 | 34 | 62 | 47 | 38 | 160 | 70 |
| Lavernder Absolute | 103 | 0 | 2 | 92 | 211 | 13 | 0 | 1 |

FIG. 3 is a series of graphs depicted in three dimensions (in a rectangular mode for the "X" and "Y" axes) showing the relative attractiveness or repellency of the materials:

tridecene nitrile;

air;

jasmine absolute (as prepared according to Example I, infra, and as defined according to the GLC profile of FIG. 7, described, supra);

dimethyl benzyl carbinyl acetate; and mixture of 81.28% mole percent geraniol and 18.72 mole percent mixture of nerol and citronellol (mole ratio of citronellol:nerol being 1.78).

The test data is for *Musca domestica L.* (Diptera:Muscidae), the housefly. The graph indicated by reference numeral 307 is the graph for the geraniol-nerol-citronellol mixture. The graph indicated by reference numeral 305 is for the dimethyl benzyl carbinyl acetate. The graph indicated by reference numeral 303 is for jasmine absolute. The graph indicated by reference numeral 302 is for air. The graph indicated by reference numeral 300 is for tridecene nitrile. The results are tabulated in Table II as follows:

TABLE II

| Composition Tested | Graph No. | Insects Collected Per Interval | | | | | | |
|---|---|---|---|---|---|---|---|---|
| Mixture of Geraniol, Nerol and Citronellol | 307 | 0 | 2 | 16 | 4 | 10 | 0 | 4 |
| Dimethyl benzyl carbinyl acetate | 305 | 0 | 44 | 20 | 14 | 58 | 13 | 15 |
| Jasmine absolute | 303 | 0 | 16 | 187 | 23 | 16 | 23 | 16 |
| Air | 302 | 0 | 4 | 11 | 5 | 5 | 5 | 385 |
| Tridecene nitrile | 300 | 0 | 10 | 23 | 8 | 1 | 10 | 2 |

FIG. 4 is a schematic cutaway elevation diagram of an extrusion and pelletizing apparatus useful in carrying out a process of our invention during the operation of said apparatus whereby the insect attractant, lavender absolute or jasmine absolute, is incorporated into a polymer such as polyethylene. Motor 15 drives the extruder screws located at 23A in barrel 16, the extruder being operated at temperatures in the range of from about 150° C. up to about 250° C. At the beginning of the barrel resin at source 12 together with additives, e.g., processing aids and densifiers at location 13 is added via addition funnel 14 into the extruder. Simultaneously (when the operation reaches "steady state"), insect attractant, lavender absolute and/or jasmine absolute is added to the extruder at one, two or more of barrel segments S-3, S-4, S-5, S-6, S-7 and S-8 of the extruder (which may be a twin screw or single screw extruder) at locations 18a, 18b, 18c and 18d (for example) by means of gear pump 23 from source 17. From source 19 into barrel segments S-5, S-6, S-7, S-8, S-9 and S-10, a gaseous or liquid blowing agent, e.g., nitrogen, carbon dioxide and the like as described, supra, are added simultaneously with the addition of insect attractant, e.g., lavender absolute, jasmine absolute or combinations of lavender absolute and jasmine absolute. The feed rate range of resin is about 80–300 pounds per hour. The feed rate range of the insect attractant is between 1 and 35% of the feed rate range of the resin. The blowing agent range is such that the pressure of the gas or the pressure over the liquid being fed into the extruder is between about 50 and 200 psig if, indeed, blowing agent is added. If desired, the extruded ribbon or cylinder may be passed through water bath 20 and pelletized in pelletizer 21 and then passed into collection apparatus 21a.

The following examples serve to illustrate processes for preparing attractants of our invention, namely, lavender absolute and jasmine absolute. These examples are not intended to be limiting, the limitation to the instant invention only being done via the claims.

EXAMPLE I

Preparation of Jasmine Absolute

400 Kilograms of jasmine flowers are extracted at a temperature of 80° C. with 18 liters of anhydrous methylene chloride. The 18 liters of anhydrous methylene chloride is intimately admixed with the jasmine flowers and refluxed at 10 atmospheres pressure for a period of 12 hours. At the end of the 12 hour period, the resulting "mash" is filtered and the filtrate is subjected to evaporation and then fractionally distilled at 0.05 mm/Hg pressure and at a temperature of 84°–86° C.

The resulting product has the GLC profile as set forth in FIG. 7.

EXAMPLE II

Production of Lavender Absolute 1,000 Grams of lavandin plant is extracted with 15 kilograms of a 50:50 mixture of anhydrous methyl alcohol and anhydrous isopropyl alcohol. The alcohol and plant material is intimately admixed in a vessel equipped with stirrer, thermometer, reflux condenser and heating apparatus. The extraction is carried out at 10 atmospheres pressure for a period of 24 hours at a temperature of 110° C. At the end of the 24 hour period, the "mash" is cooled and filtered and the resulting filtrate is evaporated and fractionally distilled at 74° C. and 0.03 mm/Hg pressure.

The resulting distillate is defined according to the GLC profiles of FIGS. 8A and 8B.

With respect to FIG. 8A, the peak indicated by reference numeral 801 is for d-limonene. The peak indicated by reference numeral 802 is for 1,8-cineol. The peak indicated by reference numeral 803 is for camphor. The peak indicated by reference numeral 804 is for dihydrolinalool. The peak indicated by reference numeral 805 is for linalyl acetate.

In FIG. 8B, the peak indicated by reference numeral 806 is for a 50:50 mixture of 1,8-cineol and limonene. The peak indicated by reference numeral 807 is for linalool. The peak indicated by reference numeral 808 is for camphor. The peak indicated by reference numeral 809 is for a 50:50 mixture of dihydrolinalool and neoalloocimene. The peak indicated by reference numeral 810 is for a 50:50 mixture of dihydrolinalyl acetate and bornyl acetate. The peak indicated by reference 811 is for lavandulyl acetate.

EXAMPLE III

Production of Lavandin Abrialis

The product of Example II is admixed with an equal volume of ethyl alcohol. The resulting mixture is placed into a reaction vessel equipped with thermometer, reflux condenser and heating mantle. To the mixture, 500 grams of carbon black is added. The resulting mixture is heated at reflux and 10 atmospheres pressure for a period of 15 hours, at reflux conditions. The resulting mixture is then cooled and filtered. The resulting product in then evaporated and fractionally distilled at 0.03 mm/Hg pressure and 80° C. The resulting product has GLC profiles as defined according to FIGS. 8C and 8D.

Referring to FIG. 8C, the peak indicated by reference numeral 812 is for α-pinene. The peak indicated by reference numeral 813 is for camphene. The peak indicated by reference numeral 814 is for β-pinene. The peak indicated by reference numeral 815 is for myrcene. The peak indicated by reference numeral 816 is for d-limonene. The peak indicated by reference numeral 817 is for 1,8-cineol. The peak indicated by reference numeral 818 is for cis-β-ocimene. The peak indicated by reference numeral 819 is for trans-β-ocimene. The peak indicated by reference numeral 820 is for n-hexyl isobutyrate. The peak indicated by reference numeral 821 is for 1-octen-3-yl-acetate. The peak indicated by reference numeral 822 is for camphor. The peak indicated by reference numeral 823 is for linalool. The peak indicated by reference numeral 824 is for a 50:50 mixture of β-caryophylene and lavandulyl acetate. The peak indicated by reference numeral 825 is for 4-terpineol. The peak indicated by reference numeral 826 is for caryophyllene oxide. The peak indicated by reference numeral 827 is for borneol.

Referring to FIG. 8D, the GLC profile for the dual-fused silica system/OV-1 column, the peak indicated by reference numeral 828 is for α-pinene. The peak indicated by reference numeral 829 is for a 50:50 mixture of camphene and β-pinene. The peak indicated by reference numeral 830 is for 1-octen-3-ol. The peak indicated by reference numeral 831 is for 40:30:30 mixture of cis-β-ocimene, cineol and limonene. The peak indicated by reference numeral 832 is for trans-β-ocimene. The peak indicated by reference numeral 833 is for linalool. The peak indicated by reference numeral 834 is for camphor. The peak indicated by reference numeral 835 is for borneol. The peak indicated by reference numeral 836 is for 4-terpineol. The peak indicated by reference numeral 837 is for linalyl acetate. The peak indicated by reference numeral 838 is for lavandulyl acetate. The peak indicated by reference numeral 839 is for geranyl acetate. The peak indicated by reference numeral 840 is for caryophyllene oxide. The peak indicated by reference numeral 841 is for β-caryophyllene.

What is claimed is:

1. A method of attracting *Aedes aegypti* to a three-dimensional space inhabitable by said *Aedes aegypti* comprising the step of exposing said three-dimensional space to an *Aedes aegypti*-attracting concentration and quantity of lavender absolute.

2. The method of claim 1 wherein the lavender absolute is contained in a polymer matrix.

3. The method of claim 2 wherein the polymer matrix is a biodegradable polymer.

4. The method of claim 3 wherein the biodegradable polymer is a polyepsilon caprolactone polymer or a polyurethane polymer.

5. The method of claim 1 wherein the lavender absolute has a composition defined according to the GLC spectra of FIGS. 8A, 8B, 8C or 8D.

6. The method of attracting *Aedes aegypti* to an insect trap comprising the step of exposing the environment surrounding said trap to an insect attractant-containing polymer which comprises a mixture of a polymer and from about 1% up to about 45% by weight of said polymer of lavender absolute.

7. The method of claim 6 wherein the lavender absolute has a composition defined according to the GLC spectra of FIGS. 8A, 8B, 8C or 8D.

* * * * *